(12) United States Patent
Strnad et al.

(10) Patent No.: US 8,167,918 B2
(45) Date of Patent: May 1, 2012

(54) ORTHOPEDIC PLATE FOR USE IN THE MTP JOINT

(75) Inventors: Lee A. Strnad, Broadview Hts., OH (US); Vinay Korlepara, Plantation, FL (US); Derek S. Lewis, Copley, OH (US); Dustin Ducharme, Stow, OH (US); Gordon Bennett, Akron, OH (US); James Sferra, Chagrin Falls, OH (US)

(73) Assignee: Orthohelix Surgical Designs, Inc., Medina, OH (US)

( * ) Notice: Subject to any disclaimer, the term of this patent is extended or adjusted under 35 U.S.C. 154(b) by 482 days.

(21) Appl. No.: 12/378,539

(22) Filed: Feb. 17, 2009

(65) Prior Publication Data
US 2009/0210010 A1 Aug. 20, 2009

Related U.S. Application Data

(60) Provisional application No. 61/066,206, filed on Feb. 19, 2008.

(51) Int. Cl.
*A61B 17/80* (2006.01)

(52) U.S. Cl. ........................................ 606/280; 606/906

(58) Field of Classification Search .......... 606/280–299, 606/70, 71
See application file for complete search history.

(56) References Cited

U.S. PATENT DOCUMENTS

| 4,219,015 A | 8/1980 | Steinemann |
|---|---|---|
| 4,493,317 A | 1/1985 | Klaue |
| D449,692 S | 10/2001 | Michelson |
| 6,565,571 B1 | 5/2003 | Jackowski et al. |
| 6,576,018 B1 | 6/2003 | Holt |
| 7,052,499 B2 | 5/2006 | Steger et al. |
| 7,108,697 B2 | 9/2006 | Mingozzi et al. |
| 7,189,237 B2 | 3/2007 | Huebner |
| 2006/0015102 A1 | 1/2006 | Toullec et al. |
| 2006/0081553 A1 | 4/2006 | Patterson et al. |
| 2006/0106387 A1 | 5/2006 | Fanger et al. |
| 2006/0173459 A1* | 8/2006 | Kay et al. .................. 606/69 |

(Continued)

FOREIGN PATENT DOCUMENTS

JP 20030102744 4/2003

(Continued)

OTHER PUBLICATIONS

VariAx Foot Locking Plate System by Stryker dated 2009 (23 pages).

(Continued)

*Primary Examiner* — Thomas Barrett
*Assistant Examiner* — Melissa A Golob
(74) *Attorney, Agent, or Firm* — Hudak, Shunk & Farine Co. LPA

(57) ABSTRACT

The present invention is a MTP plate that has a first embodiment with a profile having bilateral mirror symmetry of the about a transverse plane with an angle of about 5° for dorsiflexion and an angle of about 10° for valgus. Both ends of the plate include a central arm having a slot for compression and two offset arms having offset ears with locking screw holes that provide for multiplanar compressive fixation. The bone contacting surface of the plate is radiused to allow the plate to be in snug contact with the bone. In a second embodiment of the plate for revision surgery, the proximal end of the plate includes a metatarsal extension and the plate has a central locking hole for securing bone graft.

21 Claims, 3 Drawing Sheets

U.S. PATENT DOCUMENTS

| | | | |
|---|---|---|---|
| 2006/0235396 | A1 | 10/2006 | Sanders et al. |
| 2006/0235397 | A1 | 10/2006 | Sanders et al. |
| 2006/0241592 | A1 | 10/2006 | Myerson et al. |
| 2006/0241607 | A1 | 10/2006 | Myerson et al. |
| 2006/0241608 | A1* | 10/2006 | Myerson et al. ............ 606/69 |
| 2007/0016205 | A1 | 1/2007 | Beutter et al. |
| 2007/0073298 | A1 | 3/2007 | Beutter et al. |
| 2007/0083204 | A1 | 4/2007 | Sidebotham |

FOREIGN PATENT DOCUMENTS

| | | |
|---|---|---|
| JP | 20060280951 | 10/2006 |

OTHER PUBLICATIONS

The corresponding International Search Report and Written Opinion dated Apr. 17, 2009.

Foot Reconstructive and Trauma Surgery—Internal and External Fixation Systems May 29, 2008 (pp. 2-12).

New Trauma Products from AO Development, Jun. 2006 (pp. 1-8).

A Straight Answer for Kids, Jan. 2007 (4 pages).

* cited by examiner

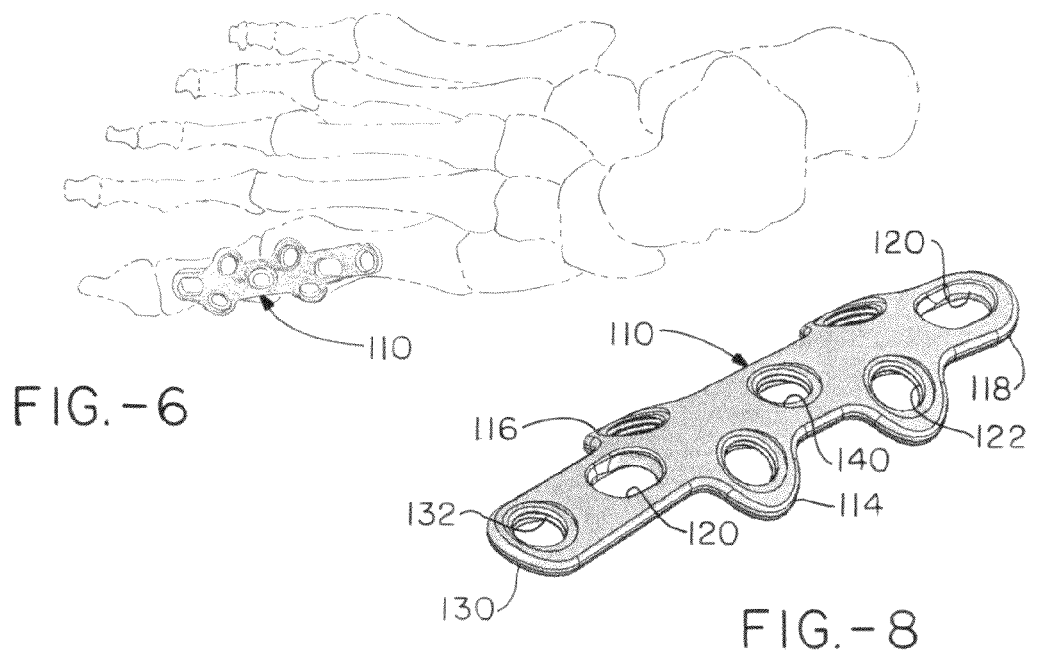
FIG.-6
FIG.-8
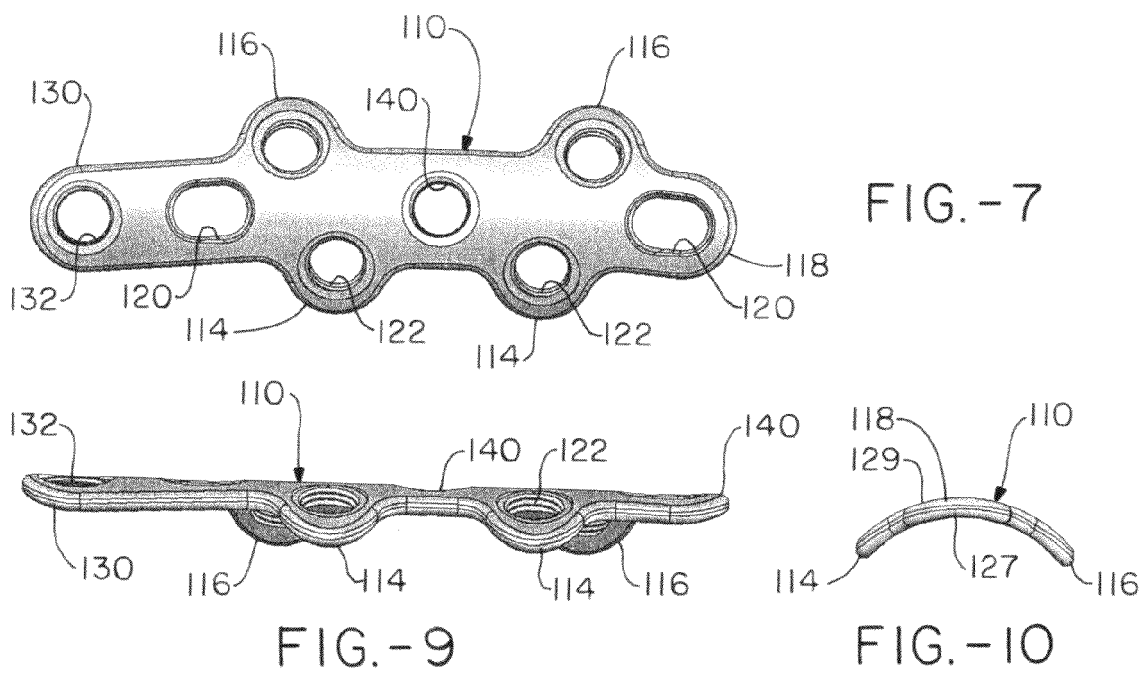
FIG.-7
FIG.-9
FIG.-10

ORTHOPEDIC PLATE FOR USE IN THE MTP JOINT

CROSS-REFERENCE

This is a U.S. patent application of U.S. Provisional Application No. 61/066,206 filed on Feb. 19, 2008 for ORTHOPEDIC PLATE FOR USE IN THE MTP JOINT which is hereby fully incorporated by reference.

FIELD OF THE INVENTION

The present invention relates to an orthopedic plate which is configured for the fixation of the bones of the first metatarsophalangeal joint including, for example, stabilization of a fracture, dislocation, fusion, or reconstruction of a deformity.

BACKGROUND OF THE INVENTION

Together the foot and ankle have over 25 bones and 33 joints along with more than 100 named muscles, tendons, and ligaments and a network of blood vessels, nerves, all residing beneath a relatively slim covering of soft tissue and skin. Structurally, the foot has three main anatomical regions: the forefoot, the midfoot, and the hindfoot. These parts work together with the ankle, to provide the body with support, balance, and mobility. A structural flaw or malfunction in any one part can result in the development of problems, which are manifested in other areas of the body.

Twenty one bones make up the front part of the foot known as the forefoot, and include five metatarsal bones, fourteen phalanges that form the toes, and two sesamoid bones. The metatarsal bones and phalanges join together at the metatarsal-phalangeal ("MTP") to form the ball of the foot. These joints play a significant role in the stability of the foot and propulsion of the lower extremity. The forefoot balances pressure on the ball of the foot and bears a substantial amount of the body weight.

The forefoot includes the five toes (which are also known as the "phalanges") and their connecting long bones (or "metatarsals"). Several small bones together comprise a phalanx or toe. Four of the five toes have three phalanx bones respectively connected by two joints. The big toe (or "hallux") has two phalanx bones distal and proximal with a joint in between called the interphalangeal joint. The big toe articulates with the head of the first metatarsal at the first metatarsophalangeal joint (the "MTP" joint) and there are two tiny, round bones called sesamoids on the plantar side of the metatarsal head. The phalanges are connected to the metatarsals at the ball of the foot. The two sesamoid bones are located underneath the first metatarsal bone and assist in flexion of the big toe at the first metatarsal-phalangeal joint.

The hallux is subject to several conditions which appear to present as deformities. For example, the first MTP joint can develop bunions, which is a term commonly used to refer to an outward protrusion on the medial side of the foot caused by the medial dislocation of the first and second metatarsal bones. The resulting bunion often is subjected to friction or pressure from shoes that cause swelling, redness, irritation, and pain along the side of the joint. In severe cases, the joint becomes dislocated and the phalanx of the big toe relocates and spirals diagonally (i.e., deviates laterally and/or rotates) toward the second toe.

It is believed that an instability in the mechanics of the first metatarsal (foot bone) phalangeal (toe bone) joint are the primary cause of this deformation which may be the result of one or more of the morphology of the foot, exercises to which the foot is subjected and the mechanics of footwear. Other causes are those that all may lead to a disruption in the balance of forces at the joint leading to a bunion formation and may include: congenital birth defects, neuromuscular disorders, rheumatoid arthritis, laxity in the ligaments, or trauma.

For some indications, the surgical treatment is limited to removal of a medial portion of the metatarsus to reduce the prominence of the bunion. In more severe cases, or for elderly patients, resectional arthroplasty of the metatarsophalangeal (MTP) joint, with or without implant, or joint arthrodesis may be indicated, although these procedures result in loss of motion at that joint. Fusion or "arthrodesis" of the MTP joint is a common procedure for treatment of severe bunions with the object of alleviating pain, restoring function or reducing the deformity, although most surgical procedures result in at least some loss of motion at the joint and fusion results in complete loss of motion at the joint.

Arthodesis is also performed for "hallux rigidus" which is a form of degenerative arthritis in which the proximal phalynx of the great toe is dislocated in dorsal flexion and in which movement of the joint is gradually restricted and often finally "frozen" over time. This condition can result from the inherited structure of the foot or from certain use-related trauma, such as constant balancing on the balls of the foot. Other indications that justify fusion of the joint include rheumatoid and post-traumatic arthritis and for revision of prior non-union surgeries.

The goal of surgical intervention is to restore acceptable hallux valgus, inter-metatarsal angle and distal metatarsal angles and to return the metatarsus and MTP joint to their optimum anatomic positions. Many of the current procedures involve removal of bone or an "osteotomy". These procedures may involve removal of bone (i.e. a closing wedge osteotomy) or insertion of a wedge of bone (i.e. an opening wedge osteotomy). The success of such procedures depends on complete fixation of bone segments.

Prior art surgical methods have included fixation using bone screws, cerclage wire, K-wire, and mono-filament wire. In some cases, a plate is used to bridge the fracture or osteotomy opening or to hold the bone fragments in position during fusion.

SUMMARY OF THE INVENTION

The present invention provides a MTP plate which is intended to span the MTP joint. The plate is provided in a first and second embodiment. The second embodiment provides for a variation on the first plate for revision surgeries, i.e. for surgeries where a first procedure has previously been performed, and in particular provides support for a bone graft. The first embodiment of the plate has bilateral mirror symmetry about a transverse plane with an angle of up to about 10° (and preferably about 5°) for dorsiflexion and an angle up to about 10° for valgus. In this embodiment, both ends of the plate include a central arm having a slot for compression toward the middle of the plate and two offset ears having locking screw holes that provide for multiplanar compressive fixation. Alternatively, the plate may include a compression slot at one end that can be used to cause compression toward the center of the plate, and a locking screw in the other end of the plate. While this destroys the bilateral mirror symmetry when the openings are taken in account, the plate outline continues to display this type of symmetry. The central portion of the plate optionally includes an opening for radiographic viewing for fusion and to allow for bone packing. The bottom surface of the plate is radiused. This allows the plate to be in snug contact with the bone. In the second embodiment, the proximal portion of the plate includes a further extension which extends further along the metatarsal bone and also has a locking hole for a further screw. The central portion of this plate includes a non-locking hole to fix graft material.

BRIEF DESCRIPTION OF THE DRAWINGS

FIG. 6 is a dorsi-medial view of a MTP joint with a second embodiment of an orthopedic plate positioned thereon in accordance with the invention;

FIG. 7 is a top view of the orthopedic plate of FIG. 6;

FIG. 8 is a top perspective of the orthopedic plate of FIG. 7;

FIG. 9 is a first side view of the plate shown in FIG. 7;

FIG. 10 is right end view of the plate shown in FIG. 7

DETAILED DESCRIPTION OF THE INVENTION

Figure 1:
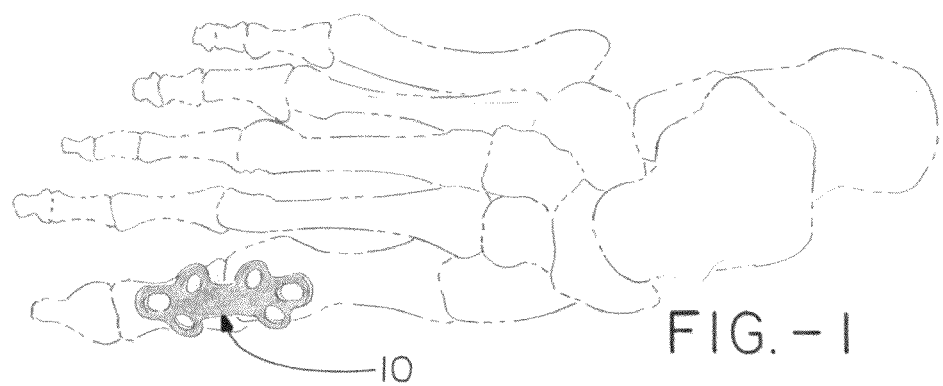
FIG. 1 is a dorsi-medial view of a MTP joint with a first embodiment of an orthopedic plate positioned thereon in accordance with the invention.

FIG. 1 shows a skeletal version of a foot from the top (i.e. a dorsal view) with the MTP plate 10 of the present invention in place between the junction of the head of the first metatarsal and the proximal phalange of the first ray (i.e. the great toe) at the first metatarsophalangeal joint. Thus. FIG. 1 illustrates the first embodiment of the plate used in fixation (i.e. for fusion) of the bones of the first MTP joint.

Figure 2:
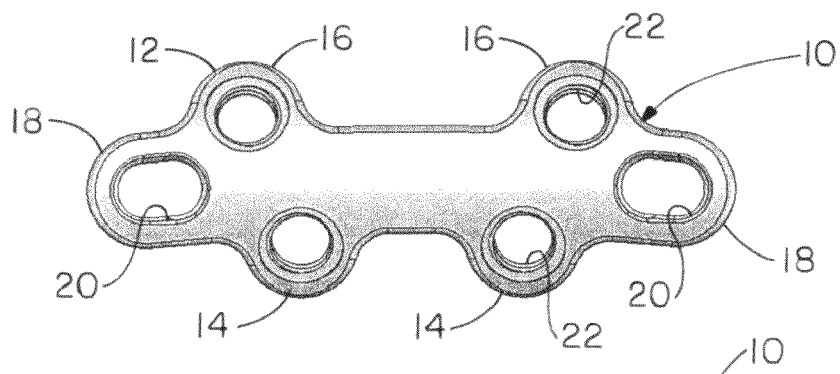
FIG. 2 is a top view of the orthopedic plate of FIG. 1.

As viewed from the top in FIG. 2, it can be seen that at each end, the plate 10 has a sets of opposing projections or ears 12 including a more central (relative to the transverse medial plane) projection 14 and a more distant projection 16 which extend away from a rounded terminal 18 portion at either end which includes a compression slot 20. Each 14, 16 of one of the central and the distant ears include a screw hole 22 (which can include internal threads so as to form a locking interface with the respective bone or bone fragment.) The central ears are on the same side of the plate relative to the midline of the plate. The distant ears are also on the same side of the plate as each other and on the opposite side of the plate of the central ears. The bottom 27 (or bone facing surface) of the plate includes a radius of between about 7 and about 15, and preferably between about 8 and about 12, and most preferably about 9 and about 11 millimeters. The two pairs of ears continue this curvature and the through holes are placed so that the angle of the longitudinal axis of the screws converges in the direction of the distal end of the screw. The screw holes are placed with the longitudinal axis perpendicular a tangent to the top surface of the ear with the effect that the longitudinal axes of the screws converge in the direction of the distil end. This increases the pull-out strength of the screws. The placement of the lateral (i.e. relative to the medial line of the body) ears both central to the mid-line of the plate allows the insertion of the plate with a smaller incision.

The screws do not in fact conflict since each of the ears in an opposing pair form a different angle to the central trunk so that the longitudinal axis of the screws are offset from each other along the length of the plate. The pre-bent configuration of the plate is designed to increase operating room efficiency by facilitating commonly desirable shapes while maintaining the required strength and by permitting bending without deforming the screw holes. This results in making customization in anticipation or during surgery easier.

The plate includes a valgus angle at the central transverse axis of between about 5° and 25°, and preferably between about 5° and about 15°, and most preferably between about 8° and about 12° As an option, the central portion of the plate between the projections, the plate can include an opening which can be used to view the placement of the plate relative to the bones as well as for adding bone graft material. The opening is preferably an oval shape, which allows the maximization of the area viewed while maintaining sufficient stiffness to hold the bones in position to allow fusion.

Figure 11:
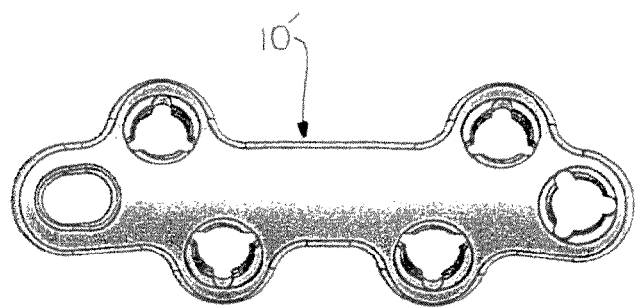
FIG. 11 is a top view of a further embodiment of the orthopedic plate of the present invention.
Figure 12:
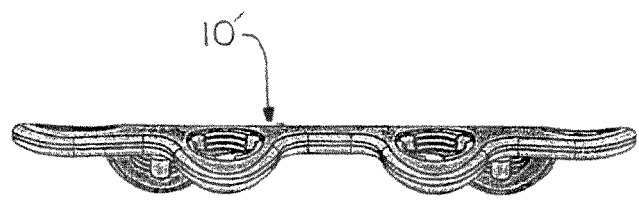
FIG. 12 is a top perspective view of the orthopedic plate of FIG. 11.

In the first embodiment, the plate displays bilateral mirror symmetry (meaning that the two ends are mirror images of each other) about a transverse central axis, and further includes an angle of between about 2° and 25°, and preferably between about 3° and about 15°, and most preferably between about 4° and about 6° to account for a dorsi-flexion in the fused area. This distinct type of symmetry allows the same plate to be used for a right or left side procedure by rotating the length of the plate 180°, as the body also includes mirror symmetry on the right and left sides. Alternatively, as shown in FIGS. 11 and 12, the plate includes a locking hole in the distal end, with a single compression slot at the other end of the plate which applies a compression in the direction of the locking hole.

Figure 4:
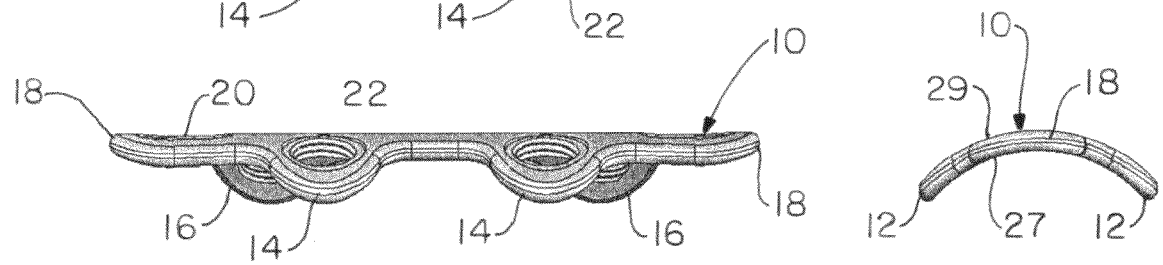
FIG. 4 is a first side view of the plate shown in FIG. 2.
Figure 5:
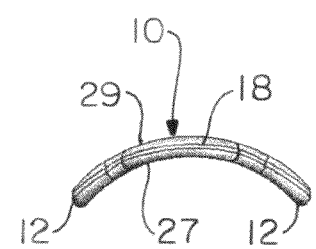
FIG. 5 is a right end view of the plate shown in FIG. 2.
Figure 3:
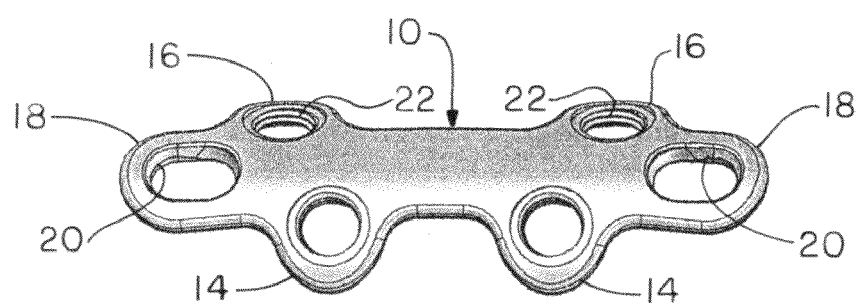
FIG. 3 is a top perspective view of the orthopedic plate of FIG. 2.

FIG. 3 shows a view of the plate in a proximal and dorsal orientation. FIG. 4 illustrates the plate from the medial side and FIG. 5 shows the plate from the end (i.e. the proximal end for the right plate). As can be seen the plate has a generally uniform thickness between the inward surface 27 which opposes and optimally, but not necessarily engages the bones, and the outward surface 29. In addition, while the inward surface 27 of the plate 10 includes a generally uniform radius of curvature along both the first and the second axis, the radius is not a continuous radius since the plate includes the dorsi-flexion angle. The compression slot includes a shoulder 24 on the internal edge 23 which tapers downward toward the transverse medial plane of the plate to drive compression toward the transverse median axis of the plate. The inclined shoulder is formed by the intersection of a obround which is cut through the thickness of the plate and a spherical cut which travels simultaneously along the length of the obround and downward through the thickness of the plate as it approaches the transverse medial plane of the plate. When the screw is inserted such that the axis of the screw is aligned with the thickness of the obround (i.e. the long axis of the screw is parallel to the walls of the obround) and such that a portion of the screw head comes in contact with the 'high' side of the slot, the incline in the slot acts to redirect a component of the axial force of the screw (which is created by the pull of the bone threads on the screw) along the length of the obround and thus causes the screw and its attached bone fragment to translate towards the transverse medial plane of the plate. The slot is oriented at an angle relative to the thickness of the plate in order to account for the intended trajectory of screw's long axis, that is, the obround is cut 'straight down' and not perpendicular to the surface of the plate because the screw is intended to be placed with it's long axis 'straight down' and not perpendicular to the axis of the plate.

Figures 13, 14:
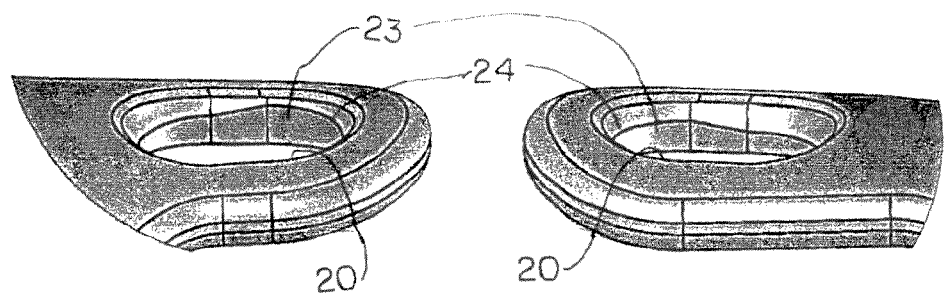
FIG. 13 is a first detailed view of the compression slot.
FIG. 14 is a second detailed view of the compression slot taken from the opposite side as FIG. 13.
Figure 15:
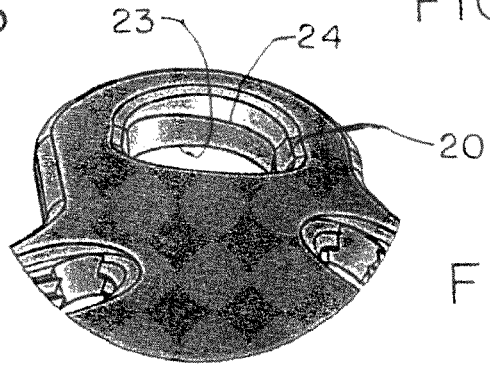
FIG. 15 is a detailed view of the compression slot as seen from the transverse axis.

The screws useful with the plate of the present invention are self-starting, self-tapping screws including the option of partial or full cannulation. The screws include a cutting end having multiple flutes, and preferably 2 or 3 flutes about a conical recess. The screws further include a partial taper of the inner diameter in the proximal end over the first several thread turns, for example over 2-8, and preferably over 3-5 turns in order to increase the fatigue life of the screw as well as providing potential physiological advantages in use. The screws further include a torque driving recess. The locking screws used in the locking holes of the present invention include external threads at the screw head that mate with the internal threads of the locking holes to lock the screw relative to the plate. Alternatively, variable angle screws and screw mechanisms can be used in the present invention that allow for the screw's head to be seated in the screw hole irrespective of the trajectory of the screw's long axis with respect to the geometry of the screw hole. In addition, advantageously, the screw holes (and even the compression slot) can include groves, or key ways as is shown in FIGS. 11 and 12 for the placement and orientation of drill guides which set the angle for the screw's long axis relative to the geometry of the plate holes. The screw to be used in the compression slot should be shaped so that the screw's head conforms to the geometry of the sloped feature in the compression slot in order to maximize surface contact between the screw head and the inclined portion of the compression slot as shown in FIGS. 13-15. In the preferred embodiment of the compression slot, the incline in the slot is created by a spherical cut which travels along the length of the obround and simultaneously travels downward through the thickness of the obround; thus, in the preferred embodiment, the screw that is to be placed in the compression slot has a screw head which is also spherically shaped and of similar size to the spherical cutout in the slot.

The plate is formed of a biocompatible material, and preferably a metal such as surgical grade stainless steel, titanium or a titanium alloy. Preferably, the plate has a thickness of between about 1 and 2 millimeters, more preferably between about 1.25 and 1.75 millimeters, and most preferably between about 1.4 and 1.6 millimeters. The plate includes a rounded continuous outer edge 40 which is defined between the top and the bottom surface. In addition, the plate 10 can include one or more small through hole sized to receive a K-wire or other similar guide wire as well as configurations for an interface with a drill guide, for example in the locking holes.

FIGS. 6 through 10 illustrate a second embodiment of the MTP plate 110 of the present invention having many of the same features and further including a proximal extension 130 for additional support on the metatarsal bone, and including a central locking hole 140 for graft material. The second embodiment or revision plate, includes the two opposing sets of ears, with the central pair 114 and the distant pair 116, each including screw holes 122 which are illustrated with optional internal threads for locking screws. The plate 110 includes a terminal portion 118 with a compression slot 120 and at a more proximal end, an extension 130 beyond the compression slot 120 that has a locking hole 132 for additional support along the metatarsal bone. Additionally, the plate includes a central hole, which can include threads, for graft material or in the event that no screw is used can be used for radiographic evaluation. The plate includes the same angles for dorsal flexion and to maintain the valgus angle as the first embodiment of the plate.

During the surgery the joints are first prepped which may include de-articulation between the two bones to be fused. While the plate is pre-contoured so as to fit most applications, it can be further bent by the surgeon as desirable to suit individual variations in anatomy or circumstance. The plate is placed and held in place, for example, via olive wire (thru compression slot). The plate is located such that all of the screws are aimed into the targeted bones and away from the joint. Pilot holes are drilled optionally using an appropriate drill guide. In order to generate compression across the fusion site, at least two screws are placed in the distal portion of the plate. Both screws should be inserted before fully tightening to avoid shifting of the plate. An appropriate pilot hole is drilled at the proximal end of the compression slot perpendicular to a line tangent to the center axis of the radius end of the slot (and parallel to the lateral edge of the slot). A non-locking screw (having a rounded rearward shoulder on the distal end of the head is inserted into the pilot hole in the slot, and as the screw is tightened, it will drive compression toward the fusion site. The remaining screw holes are filled in. Any wires are removed, and the plate is viewed radiographically. The soft tissues are closed in a usual layered manner.

While in accordance with the patent statutes the best mode and preferred embodiment have been set forth, the scope of the invention is not limited thereto, but rather by the scope of the attached claims.

What is claimed is:

1. A plate which is capable of fixation, using an associated screw, of bone at the first metatarsophalangeal joint comprising a plate extending along a length and having a first end and a second end and having a transverse medial plane there between, at least one of the first and the second end including a terminal area with
    a compression slot and opposing first and second ears, the first and second ears each having a threaded through hole, the compression slot including an internal edge which has an incline which tapers downward toward the transverse medial plane and to allow the associated screw to drive compression in the bone toward the transverse medial axis of the plate, and the compression slot being terminal relative to the length of the plate and to the threaded through hole of the first and second ears, and the plate having an inner surface which includes a first axis and a second axis and the first and second axes being at an angle of from about 2° to about 25° to each other in the dorsal direction and in the valgus direction, wherein the plate has a transverse central axis about which the plate displays mirror symmetry.

2. A plate as set forth in claim 1 wherein the opposing ears on the first end and the opposing ears on the second end are offset to each other relative to the length of the plate.

3. A plate as set forth in claim 2 wherein the plate further includes a central opening.

4. A plate as set forth in claim 1 wherein the first and second axes are at an angle of from about 5° to about 15° in the valgus direction.

5. A plate as set forth in claim 4 wherein the first and second axes are at an angle of from about 8° to about 12° in the valgus direction and from about 5° to about 15° in the dorsal direction.

6. A plate as set forth in claim 1 wherein the first and second axes are at an angle of from about 4° to about 10° in the dorsal direction.

7. A plate as set forth in claim 1 wherein the terminal area further comprises a threaded screw hole.

8. A plate as set forth in claim 1 wherein one of the first or second ends includes an extension.

9. A plate as set forth in claim 8 wherein the extension further includes a locking hole.

10. A plate as set forth in claim 9 wherein the plate has a thickness and the incline that slopes downward toward the transverse medial axis of the plate is formed by the intersection of an obround having a length and which is cut through the thickness of the plate and a spherical cut which travels simultaneously along the length of the obround and downward through the thickness of the plate as it approaches the transverse medial plane of the plate.

11. A plate as set forth in claim 10 wherein the central opening includes internal threads.

12. A plate system which is capable of fixation of bone at the first metatarsophalangeal joint comprising a plate, at least one locking screw having a set of distal threads and a set of proximal threads which mate with a set of threads in an opening in the plate, and optionally at least one non-locking screw which has a set of distal threads and a head having a rounded distal surface, the plate consisting of a trunk portion and a first set of ears and a second set of ears, the trunk portion extending along a length and having a first end and a second end and having a transverse medial plane therebetween, at least one of the first and the second end including a terminal area with a compression slot including an internal edge which has an incline which tapers downward toward the transverse medial plane and to allow a non-locking screw to drive compression in the bone toward the transverse medial axis of the plate, the trunk portion having a first side along the length and a second side along the length, one set of ears extending from the first side of the plate, and the second set of ears extending from the second side of the plate, each set of ears comprising a first and a second ear each having a through hole, the compression slot being terminal relative to the length of the plate to the threaded through hole of the first and second ears, and the plate having an inner surface which includes a first axis and a second axis and the first and second axes being at an angle of from about 2° to about 25° to each other in the dorsal direction and in the valgus direction.

13. A plate system as set forth in claim 12 wherein the plate has a transverse central axis about which the plate displays mirror symmetry.

14. A plate system as set forth in claim 12 wherein the opposing ears on the first side and the opposing ears on the second side are offset to each other relative to the length of the plate.

15. A plate system as set forth in claim 14 wherein the first and second axes are at an angle of from about 8° to about 12° in the valgus direction and from about 5° to about 15° in the dorsal direction.

16. A plate system as set forth in claim 15 wherein the first and second axes are at an angle of from about 4° to about 10° in the dorsal direction.

17. A plate system as set forth in claim 12 wherein one of the first or second ends includes an extension with a locking hole.

18. A plate as set forth in claim 8 wherein the through hole in the first ear and the through hole in the second ear each include internal threads.

19. A method of fusing a first metatarsophalangeal joint, comprising:
surgically accessing the joint by making an incision;
selecting a plate system comprising a locking screw having at least one locking thread having a set of distal threads and a set of proximal threads which mate with a set of threads in an opening in the plate, and at least one non-locking screw which has a set of distal threads and a head having a rounded distal surface, the plate comprising a trunk portion and a first set of ears and a second set of ears, the trunk portion extending along a length and having a first end and a second end and having a transverse medial plane therebetween, at least one of the first and the second end including a terminal area with a compression slot including an internal edge which has an incline which tapers downward toward the transverse medial plane and to allow the non-locking screw to drive compression over the first metatarsophalangeal joint toward the transverse medial axis of the plate, the trunk portion having a first side along the length and a second side along the length, one set of ears extending from the first side of the plate, and the second set of ears extending from the second side of the plate, each set of ears comprising a first and a second ear each having a threaded through hole, the compression slot being terminal relative to the length of the plate to the threaded through hole of the first and second ears, and the plate having a inner surface which includes a first axis and a second axis and the first and second axes being at an angle of from about 2° to about 25° to each other in the dorsal direction and in the valgus direction;
selectively drilling a pilot hole for at least one of the locking screws and inserting a screw through a threaded hole in an ear in the plate and into the pilot hole;
selectively drilling a pilot hole for at least one of the non-locking holes and inserting the non-locking screw through the compression slot and into the compression slot pilot hole to drive compression at the joint; and
surgically closing the incision.

20. A plate as set forth in claim 12 wherein the plate has a thickness and the incline that slopes downward toward the transverse medial axis of the plate is formed by the intersection of an obround having a length and which is cut through the thickness of the plate and a spherical cut which travels simultaneously along the length of the obround and downward through the thickness of the plate as it approaches the transverse medial plane of the plate.

21. A plate as set forth in claim 19 wherein the plate has a thickness and the incline that slopes downward toward the transverse medial axis of the plate is formed by the intersection of an obround having a length and which is cut through the thickness of the plate and a spherical cut which travels simultaneously along the length of the obround and downward through the thickness of the plate as it approaches the transverse medial plane of the plate.

* * * * *